United States Patent [19]
Kruse

[11] Patent Number: 5,651,831
[45] Date of Patent: Jul. 29, 1997

[54] PROCESS FOR IMMOBILIZING ORGANIC AND INORGANIC POLLUTANTS IN A CONTAMINATED SOIL MATERIAL ON A REMEDIATION SITE

[76] Inventor: Kai Kruse, Rheinallee 8a, D-53579 Erpel/Rh., Germany

[21] Appl. No.: 232,112
[22] PCT Filed: Sep. 3, 1993
[86] PCT No.: PCT/CH93/00217
  § 371 Date: Jul. 1, 1994
  § 102(e) Date: Jul. 1, 1994
[87] PCT Pub. No.: WO94/05438
  PCT Pub. Date: Mar. 17, 1994

[30] Foreign Application Priority Data

Sep. 4, 1992 [CH] Switzerland ............ 2782/92

[51] Int. Cl.$^6$ ............................................ B08B 7/04
[52] U.S. Cl. ..................... 134/18; 134/25.1; 558/252
[58] Field of Search ................ 134/25.1, 18; 210/772, 210/751; 558/252, 259

[56] References Cited

U.S. PATENT DOCUMENTS 4,473,477 9/1984 Beall ........................ 210/691

FOREIGN PATENT DOCUMENTS 0192954 9/1986 European Pat. Off. .

OTHER PUBLICATIONS

Sims, "Soil Remediation Techniques at Uncontrolled Hazardous Waste Sites", J. of the Air and Waste Managment Association, May 1990, vol. 40, No. 5, pp. 704–729.
Stinson, "EPA Site Demonstration of the International Waste Technologies/Geo–Con In Situ Stabilization/Solidification Process", J. of the Air and Waste Managment Ass, vol. 40, No. 11, Nov. 1990, pp. 1569–1576.
Wolf "Adsorption of Organic Pollutants on Montmori Nonite Treated with Amines", J. of the Water Pollution Control Federation, vol. 58, No. 1, Jan. 1986, pp. 68–76.

*Primary Examiner*—Zeinab El-Arini

[57] ABSTRACT

A process for immobilizing organic and inorganic pollutants in contaminated soil materials in which partial remediation areas of a reconstruction site are purified by an on-site procedure presenting no danger to the surrounding ground water. With a clay mineral content of greater than or equal to 60 wt. %, both organic and inorganic pollutants are reduced and immobilized by washing with an alkylammonium compound. When the clay mineral content is less than 60 wt. %, a bentonite compound is added in controlled amounts and the pollutants are immobilized or further washed out.

11 Claims, 1 Drawing Sheet

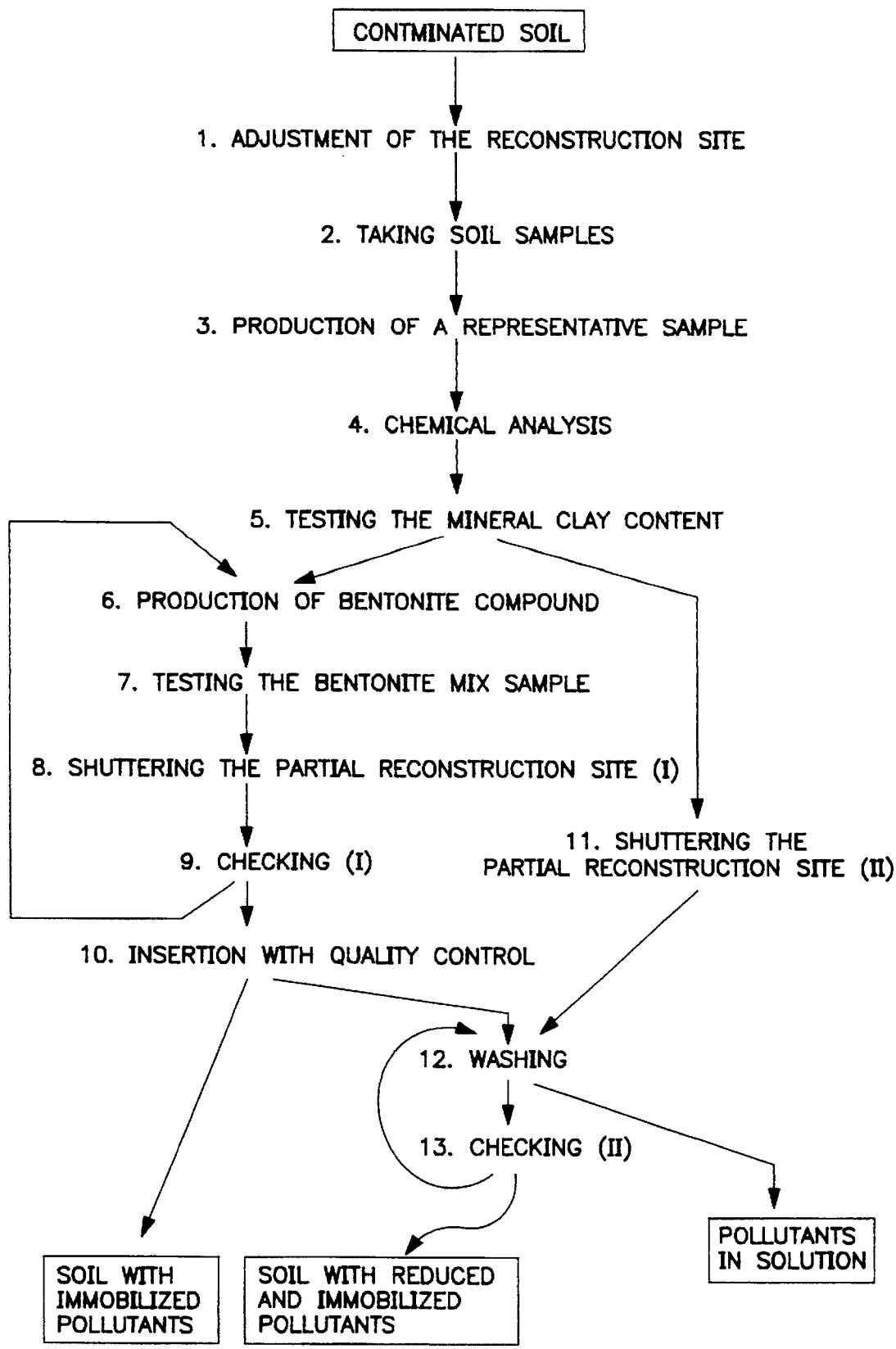

PROCESS FOR IMMOBILIZING ORGANIC AND INORGANIC POLLUTANTS IN A CONTAMINATED SOIL MATERIAL ON A REMEDIATION SITE

BACKGROUND OF THE INVENTION

The present invention provides a process for immobilizing organic and inorganic pollutants in contaminated soil materials of a remediation site.

It is state of the art that swelling clay materials are used for adsorbing heavy metal ions in wastewater treatment systems and that organo-bentonites which have high adsorption properties are used to upgrade landfill barriers.

U.S. Pat. No. 4,473,477 describes a process for the controlled storage of materials containing organic pollutants, which are bonded for adsorption into an organophilic bentonite (organoclay). To this end, an organophilic bentonite is used to bind liquid or solid contaminated organic material. It is of disadvantage that the whole landfill body must be treated with organophilic bentonite, or that leachate is pumped through a filter pad of organophilic bentonite, or that a layer of pure organophilic bentonite be used as landfill sealing. The use of large quantities of organophilic bentonite for this purpose is uneconomical.

Moreover, it is known that barrier material with too high permeability and too small cation exchange capacity or with too little heavy metal adsorption can be improved by adding a swelling clay, e.g. a bentonite treated with S-trimercaptotriazine in the form of sodium salt. This can be done by forced mixing or countersinking or by injection. This permits to achieve quadruple adsorption as compared to a conventional Ca-bentonite. In addition, the swelling effect of the Na-ions becomes effective, causing a substantial reduction of the permeability coefficient which remains constant even after exchanging the heavy metal ions for the Na-ions because the remaining swelling clay materials will exchange these excess Na-ions.

Furthermore, for immobilizing pollutants in soils, bonding processes are known by which the contaminated soil is bonded with e.g. cement. The so consolidated soil is no longer a soil proper but a concrete-like body which cannot be worked any more with the customary foundation engineering equipment, and this has a disadvantageous effect.

When using chemicals for immobilization a frequent disadvantage is their toxicity, and so their handling will cause new contaminations. In case of conventional flushing processes, the pollutants are obtained in diluted form and partly in large quantities because of the long treatment periods. In addition, a conventional flushing is practicable only for the coarse fractions and not for the fine fractions. Apart from that, no immobilization of the remaining pollutants is achieved by means of this flushing method.

It is the task of the present invention to provide a process in which a soil material contaminated with pollutants is treated with a specific addition of clay which causes an immobilization of existing pollutants and/or in which the pollutant content is reduced by flushing.

SUMMARY OF THE INVENTION

According to the invention, this task is solved by means of a process for immobilizing organic and inorganic pollutants in a contaminated soil material of a remediation site. According to one aspect of the process, a remediation site is subdivided in partial remediation areas (i) from which representative samples P (i) are prepared and chemically analyzed, while determining and checking a clay mineral content.

The partial remediation areas (i) are excavated, washed and verified dependent on the clay mineral content, whereby a soil material with reduced and immobilized pollutants and a pollutant solution are obtained.

The partial remediation areas are excavated (i) when the pre-measured clay mineral content is, for example, 60 wt % or more. The washing is preferably performed using an alkyl ammonium solution, and can be repeated several times until the specified requirements have been met.

According to another aspect of the inventive process, the remediation site is subdivided into partial remediation areas (i). From these partial remediation areas, representative samples P(i) are prepared and chemically analyzed, while determining and checking a clay mineral content.

A bentonite formulation is developed for each partial remediation area (i) and a bentonite mixing sample is prepared and tested, wherein such partial remediation areas (i) are excavated and tested. A quality-controlled insertion is applied, whereby a soil material with immobilized pollutants or, by means of a washing, a soil material with reduced and immobilized pollutants and a pollutant solution are obtained.

A bentonite formulation can be prepared for each partial remediation area (i) when the pre-measured clay mineral content is, for example, less than 60 wt %. In the event that the result after retesting is inadequate, a modified bentonite formulation can be developed.

In case of inadequate quality control, a washing with an alkyl ammonium solution can be carried out. Moreover, the washing can be repeated several times until the specified requirements of quality control are met.

The inventive process has applicability to the treatment of abandoned contaminated sites containing organic and inorganic pollutants at the same time.

BRIEF DESCRIPTION OF THE DRAWINGS

The FIGURE includes a flowchart depicting a process for immobilizing pollutants in contaminated soil material according to the present invention

DETAILED DESCRIPTION OF THE INVENTION

The processes of the invention are explained in more detail with reference to the flowsheet (FIGURE), while the FIGURE shows the general steps. To describe the different process steps, those reference numbers of the flowsheet are used that are indicated to classify the individual steps. An embodiment of it is described as example.

The term soil material comprises on the one hand solid soil material in the pedological sense and on the other backfill material such as e.g. concrete residues, gravel and tailing material as well as fillings of any kind.

The figure shows the flowsheet for a process according to which a soil material contaminated with pollutants is washed or upgraded with a clay material and also washed if necessary. This process is described below by steps 1–13.

1. Subdivision of the remediation site.

Depending on the pre-measured composition of pollutants, the whole remediation site is subdivided into partial remediation areas of a size of for example 20×20 m, which are marked 1 to i. The more homogeneous the pollutant composition, the larger the partial areas that may be chosen. In case of a very homogeneous pollutant composition, a subdivision may even become unnecessary in the marginal case, with i then equalling 1.

2. Soil material sampling.

Soil material samples are taken from the individual partial remediation areas, namely for example 8 samples P' (I) from a depth of 0.5 m and 8 samples P" (I) from a depth of 1.0 m.

3. Preparation of a representative sample.

From the 8 samples P' (I) and P" (I) each taken according to step 2, a representative sample P (i) to be allocated to the i-th partial remediation area is obtained by blending.

4. Chemical analysis.

Each of the samples P (i) is analyzed to determine the type of organic and inorganic pollutants and their concentrations. This is commonly done from an analysis of the dry substance and from eluate tests such as for example the DEV-S4 in Germany. Additionally, type and amount of clay materials contained in each sample P (i) are determined and this allows the determination of clay mineral content.

5. Checking the clay mineral content.

If the clay mineral content determined in step 4 is below 60 wt %, the procedure is continued by applying steps 6–10 or 6–10, 12 and 13, if it is 60 wt % or more, the procedure is continued by applying steps 11–13.

6. Developing the bentonite formulation.

Based on the results of the chemical analysis obtained in step 4, a special bentonite formulation is developed, comprising an addition of Ca-bentonite, an organo-bentonite or a special heavy metal absorbing bentonite such as Silitonit (available from Südchemie, München). The criteria used for developing the formulation are characteristic parameters such as the k-value (permeability coefficient), cation exchange capacity, pollutant composition and mineral content of the soil material.

7. Testing the bentonite mixing sample.

The mixing sample of contaminated soil material and bentonite prepared according to the recipe of step 6, is tested in the laboratory for its suitability, using as criteria for example soil mechanical tests, eluate tests (to DIN 38414-S4) or a leaching test (to DEV-S4).

8. Excavating partial remediation areas (I)

As soon as a suitable formulation as per step 7 is available for each of the partial remediation areas, the latter are excavated according to known practice, and the formulation is mixed in a mixed-in-plant procedure.

9. Verification (I)

The results for compliance with specified standards are verified, i.e. they are compared to the pollutant parameter list, for instance the Holland list or the Berlin list (Official Gazette for Berlin, volume no. 65, 40th year. 26 Dec. 1990, Valuation Criteria for the Judgement of Contaminated Sites in Berlin) or similar reference documents.

In case the verification in step 9 has turned out positive, the procedure is continued by applying step 10.

If the verification in step 9 has turned out negative, i.e. the specified standards have not been met or only partially, the bentonite formulation in step 6 is modified.

10. Insertion with quality control.

If the verification as per step 9 has been completed with positive results, i.e. the specified standards have been met, insertion or remediation respectively of the partial remediation area is carried out according to the formulation developed and under continuous quality control (soil engineering control), and after completed remediation, this will yield a soil material upgraded with bentonite and containing the immobilized pollutants. If quality control turns out negative, a washing procedure according to step 12 is performed.

11. Excavating partial remediation areas (II).

When a clay mineral content of 60 wt % or more is determined in step 4 for a partial remediation area, the latter is excavated according to known practice.

12. Washing

Washing of the contaminated soil material after completion of steps 1–5 and step 11 or of the contaminated soil material already upgraded according to steps 1 to 10, is carried out with an alkyl ammonium solution. On the one hand, this will reduce the pollutant content in the soil material/clay system by exchanging, among other things, the pollutants for the alkyl ammonium ions, and on the other hand, the remaining pollutants are more strongly fixed so that the soil material/clay mixture can be eluted only to a negligible extent. A slightly concentrated pollutant solution will be obtained during this washing procedure.

13. Verification (II)

The efficiency of this washing procedure will be verified by eluate tests (to DEV-S4) If the washing efficiency is sufficient, an upgraded and washed soil material is now available containing the pollutants after considerable reduction and immobilization by the washing process. If the washing efficiency is inadequate, the efficiency is improved by means of a repeated washing (step 12).

After the remediation site (step 1) has been subdivided, the application of process steps can be different for each partial remediation field. For instance, the number of washing steps (step 12) may vary, or different bentonite formulations (step 6) may have to be developed until the verification (step 9) yields an acceptable result.

The process described in steps 1–13 stands out for the following advantages:

a) An optimal clay material mixture can be added to any given composition of pollutants.

b) The soil material/clay mixture can be inserted with proctor density (DIN 18127), with no danger for the surrounding medium (groundwater).

c) The addition of clay materials and the subsequent washing with an organic solution permits on the one hand reduction of the pollutant content in the soil material/clay and on the other, to strongly fix the remaining pollutants.

d) Thus a possible dumping on a special waste landfill can be avoided because the minimal elutability will necessitate a dumping on a Class 2 or 3 landfill only (Procedure and General Conditions for the Remediation of Abandoned Contaminated Sites in the Federal Republic of Germany, MuA Lfg. 4/88, p. 282 et seq. Disposal of Waste by Deposition; Editor: Federal Environment Authority, Berlin).

The following example describes an embodiment of the described process with steps 1–5 and 11–13.

A remediation site of appr. 1800 $m^3$ was subdivided into 5 partial remediation areas of 300–400 $m^2$ each (step 1). From each of these 5 partial remediation areas, 6 soil material samples were taken each at depths of 0.4 m and 0.8 m (step 2), and a representative sample P(1) . . . P(5) for each of the partial remediation areas was prepared therefrom (step 3) and subsequently tested in a chemical analysis for inorganic and organic pollutants (step 4). Sample P(1) showed an increased concentration of zinc (64 ppm). For the organic pollutants, no increased concentrations were found. The analysis of the clay materials showed the following composition (in wt %) for sample P(1): montmorillonite 54.8%, kaolinite 27%, illite 5.2%, carbonate 1%, quartz 12%. From these percentages, a sum of 87 wt % (step 5) resulted as clay mineral content so that no addition of clay material was necessary, and the partial remediation area (1) was excavated according to usual practice (step 11). The sample material obtained P(1) was mixed with a 0.5 mmol dioctadecyl ammonium bromide solution at a 1:50 (weight portions) ratio by stirring and subsequently filtering (step 12). The filtrate obtained was a pollutant solution in which still 12 ppm zinc were determined. The filter residue obtained was an 'organobentonite' which was compared to a commercial product (adsorption of diethyl ketone), while no significant differences in the adsorption behavior (related to diethyl ketone) could be determined between the two products. To verify the efficiency of this washing process (step 13), the 'organobentonite' was desorbed using the strong complexing agent EDTA (0.01 m EDTA solution), which resulted in a desorption concentration of 13 ppm zinc. This means a much smaller value (maximum permissible value less than 1 ppm) for the eluate test to DEV-S4 so that there is reason to classify the material as a soil material with immobilized pollutants. Samples P(2) . . . P(5) were handled in an analogous manner which led to similar results.

It is an essential feature of the invention that every partial remediation area can be optimally remedied by on-site application representing no danger for the surrounding medium (groundwater).

With a clay mineral content of 60 wt % or more both organic and inorganic pollutants are reduced and immobilized by washing with an alkyl ammonium compound performed at most several times.

With a clay mineral content of less than 60 wt %, the controlled insertion of bentonite prepared according to a developed formulation is applied, and the pollutants are thus immobilized or at most further washed out.

The process is particularly suited for the remediation of abandoned contaminated sites containing organic and inorganic pollutants at the same time.

What is claimed is:

1. A process for immobilizing organic and inorganic pollutants in contaminated soil material of a remediation site, comprising defining within the remediation site one or more remediation areas; chemically analyzing at least one soil sample from each remediation area to determine a clay mineral content in each remediation area; preparing a bentonite formulation for each remediation area dependent on the clay mineral content thereof, the bentonite formulation being effective for immobilizing pollutants in the contaminated soil; excavating soil from each remediation area dependent on the clay mineral content thereof; mixing respective bentonite formulations with the excavated soil to obtain a soil material having immobilized pollutants; and optionally, following said mixing, washing the excavated soil/bentonite mixture to obtain a soil material with reduced and immobilized pollutants and a pollutant solution.

2. The process of claim 1, wherein the bentonite formulation preparation and the soil excavation are performed when the clay mineral content of a respective remediation area is less than 60 wt. %.

3. The process of claim 1, further comprising washing the excavated soil material/bentonite mixture with an alkyl ammonium solution to reduce pollutant content.

4. The process of claim 1, further comprising performing said excavated soil/bentonite mixture washing repeatedly until a desired pollutant immobilization has been achieved.

5. The process of claim 1, further comprising preparing a modified bentonite formulation and adding said modified formulation to said soil material having immobilized pollutants.

6. The process of claim 1 wherein said remediation site is an abandoned remediation site.

7. A process for immobilizing organic and inorganic pollutants in contaminated soil material of a remediation site, comprising defining within the remediation site one or more remediation areas; chemically analyzing at least one soil sample from each remediation area to determine a clay mineral content in each remediation area; excavating and washing the soil from the remediation areas dependent on the clay mineral content thereof, to obtain a soil material with reduced and immobilized pollutants, and a pollutant solution.

8. The process of claim 7, wherein the excavation and the soil washing are performed when the clay mineral content of a respective remediation area is 60 wt. % or more.

9. The process of claim 7, wherein the soil washing comprises washing the soil material with an alkyl ammonium solution to reduce pollutant content.

10. The process of claim 7, wherein said remediation site is an abandoned remediation site.

11. The process of claim 7, wherein the soil washing is repeated until a desired pollutant immobilization has been achieved.

\* \* \* \* \*